United States Patent [19]

Osipow et al.

[11] 4,328,319

[45] May 4, 1982

[54] PROCESS FOR PREPARING PROPELLANT COMPOSITIONS FORMING FOAMED STRUCTURES CONTAINING OPEN AND/OR CLOSED CELLS

[75] Inventors: Lloyd I. Osipow, New York, N.Y.; J. George Spitzer, Palm Beach, Fla.

[73] Assignee: Restech Research Limited Partnership, New York, N.Y.

[21] Appl. No.: 200,665

[22] Filed: Oct. 27, 1980

[51] Int. Cl.$^3$ .............................. C08J 9/12; C08J 9/26; C08J 9/30

[52] U.S. Cl. .......................................... 521/78; 52/298; 106/122; 106/170; 128/272; 132/DIG. 3; 264/53; 264/DIG. 16; 264/DIG. 17; 424/68; 424/70; 521/79; 521/88; 521/98; 424/78; 252/91

[58] Field of Search .............................. 521/78, 98, 79; 260/34.2, 29.6 PM

[56] References Cited

U.S. PATENT DOCUMENTS

| | | | |
|---|---|---|---|
| 3,572,330 | 3/1971 | Gander | 521/78 |
| 3,705,669 | 12/1972 | Cox et al. | 521/78 |
| 3,912,665 | 10/1975 | Spitzer et al. | 521/78 |
| 3,912,666 | 10/1975 | Spitzer et al. | 521/78 |
| 3,912,667 | 10/1975 | Spitzer et al. | 521/78 |

Primary Examiner—Morton Foelak

[57] ABSTRACT

A process is provided for preparing propellant compositions including a film-forming synthetic polymer that are capable of forming foamed structures containing open and/or closed cells, which may optionally contain a material which is deposited in the pores and/or walls of the structure as the structure is formed, which comprises coating the synthetic polymer in particulate form with an inert solid material insoluble in the propellant and in solutions of the synthetic resin the propellant at atmospheric temperature; and then adding the propellant and dissolving the synthetic polymer in the propellant. The process is of particular application for preparing such synthetic polymer-propellant compositions in situ in closed containers capable of withstanding an internal pressure sufficient to keep the propellant in the liquid phase at atmospheric temperature, and when the composition is withdrawn from the container to atmospheric pressure, the propellant volatilizes rapidly and a foamed structure is formed within a few seconds.

36 Claims, No Drawings

PROCESS FOR PREPARING PROPELLANT COMPOSITIONS FORMING FOAMED STRUCTURES CONTAINING OPEN AND/OR CLOSED CELLS

A propellant is defined by the Chemical Specialties Manufacturers' Association as a liquefied gas with a vapor pressure greater than atmospheric pressure at a temperature of 105° F. A large class of organic compounds falls in this category, of which some are hydrocarbons, but most are halogenated hydrocarbons having one or two carbon atoms, and one or more chlorine, fluorine or bromine atoms. Frequently different halogens are substituted in the same molecule to impart the desired vapor pressure.

Because of their high volatility propellants have been used as pore-forming agents in the production of plastic forms for many years. Propellants are soluble in many synthetic resins, and accordingly can be absorbed in the solid resin, which is desirably in particulate form, after which the resin containing the absorbed propellant is subjected to heat and pressure. The propellant vaporizes, and a closed cell foam structure is formed. U.S. Pat. No. 3,335,101 shows application of this process to the production of foams of chlorinated polyethylene. U.S. Pat. Nos. 2,387,730, 2,948,665, and 3,351,569 foam polyethylene and polypropylene in this way; U.S. Pat. No. 3,160,688 foams polystyrene; U.S. Pat. No. 3,352,802 foams polyvinyl chloride; U.S. Pat. No. 3,253,967 foams polyoxymethylene, and U.S. Pat. No. 3,305,497 foams polyurethanes. U.S. Pat. No. 3,310,617 foams a variety of thermoplastic resins by a similar but modified process intended to ensure that the propellant is uniformly dissolved or dispersed in the molten resin, so as to overcome the poor mixing problems of prior procedures.

In these procedures the amounts of propellants used are rather small, because only small amounts of the propellant can be absorbed in the solid resin, and the resin is molten, to facilitate foaming of the structure when the propellant is volatilized in situ to form the cells. The resin is then allowed to solidify before the structure can collapse, so as to preserve the foamed nature.

Randa, U.S. Pat. No. 3,072,583, patented Jan. 8, 1963, prepares foamed articles by extruding a perfluorocarbon resin in molten form, and containing from 0.1% to 5% by weight of a fluoromethane. The fluoromethane dissolves in the resin at atmospheric pressure and room temperature, and is volatilized under the extrusion conditions so as to produce a foamed structure. This procedure is useful for coating wire with a foamed coating.

Raley and Skochdopole, U.S. Pat. No. 3,379,802, patented Apr. 23, 1968, describe a similar procedure for aliphatic olefin polymer blends, and U.S. Pat. No. 3,067,147 makes cellular polyethylene using 1,2-dichloro-1,1,2,2-tetrafluoroethane.

It has also been proposed that ultramicrocellular fibers be prepared with the aid of propellants. Blades and White, U.S. Pat. Nos. 3,227,664 and 3,227,784, patented Jan. 4, 1966, describe a flash extrusion process for this purpose. Supple, ultra microcellular shaped structures are obtained from synthetic organic crystalline polymers by heating a confined mixture of the polymer plus at least one activating liquid at a temperature and pressure at which a homogeneous solution is formed, the temperature being greater than the normal boiling point of the liquid. This solution is then extruded abruptly to a region of substantially lower pressure and temperature under such conditions that a very large number of bubble nuclei exist at the extrusion orifice. Vaporization of the activating liquid rapidly cools the solution to the temperature at which the polymer precipitates and freezes in the polymer orientation produced in the rapid extrusion and expansion process.

The activating liquids must meet a number of requirements, of which one of the most noteworthy is that the liquid should dissolve less than 1% of the polymeric material at or below its boiling point. In other words, it is a nonsolvent for the polymer at or below its boiling point, but a solvent for the polymer under the extrusion conditions. To provide bubble nuclei at the instant of extrusion, a particulate solid nucleating agent can be incorporated in the polymer solution. Silica aerogel is a suitable nucleating agent. The result is a structure having extremely small closed cells. Modifications of this process are described in U.S. Pat. Nos. 3,081,519 to Blades et al, dated Mar. 19, 1963, 3,375,211 and 3,384,531 to Parrish, dated Mar. 26, 1968 and May 21, 1968, 3,375,212 to Bonner, issued Mar. 26, 1968, 3,461,193 to Gilardi, dated Aug. 12, 1969, and 3,467,744 to Woodell, dated Sept. 16, 1969.

Certain synthetic resins are soluble in propellants at room temperature. Bunting, U.S. Pat. No. 2,716,637, patented Aug. 30, 1955, pointed out that when such solutions are volatilized quickly, fine bubbles of plastic resin are obtained, which initially retain sufficient solvent so as to possess a surface tackiness, but as the solvent continues to escape from the globules, they blister and acquire an unsatisfactory appearance. Bunting avoids this by combining a fatty acid with the resin propellant solution, and keeps the resin content of the solution rather low, within the range from 5 to about 12%. Similar compositions are described by Hochberg and Pellerano, U.S. Pat. No. 2,773,855, patented Dec. 11, 1956, and these workers point out that the particles obtained are in the form of small, hollow or solid semispheres ranging from 1/16 or ¼ inch in largest dimension. Coherent foamed masses are not obtained.

Gander, U.S. Pat. No. 3,419,506, patented Dec. 31, 1968, prepares a protective film covering or dressing for wounds by dispensing from a pressurized container a composition comprising a film-forming vinyl acetate polymer or alkyl acrylate polymer, from 10 to 50% by weight based on the solids of a finely-divided filler, and a propellant, the solution having a viscosity of at least 1000 cp at normal room temperature. The inert filler must be present in order to obtain satisfactory foamed application of the film-forming resin, according to Gander, the filler perhaps serving as a nucleating agent, as described by Blades et al in U.S. Pat. Nos. 3,227,784 and 3,227,664, and rather thin, tacky films are obtained, several mils in thickness.

Spitzer et al U.S. Pat. No. 3,912,667, patented Oct. 14, 1975, provides synthetic polymer-propellant compositions which comprise a film-forming synthetic polymer in an amount within the range from about 10 to about 60% by weight of the composition in solution in a liquid propellant boiling below 45° F. at atmospheric pressure and retained in the composition in the liquid phase at a superatmospheric pressure, the propellant being in a sufficient amount within the range from about 20 to about 70% by weight of the composition to form upon rapid volatilization of the propellant at atmospheric temperature and pressure a coherent, voluminous foamed structure containing open and/or closed cells; and dispersed or dissolved in the composition an additive in an amount within the range from about 5 to about 700% by weight of the polymer, in excess of the amount soluble in the polymer in the absence of the propellant, and which is deposited in the cells of the structure when the propellant volatilizes, and which can be removed from the cells of the structure, any organic liquid present which is a solvent for the polymer and boils at or above 45° F. at atmospheric pressure being in an amount from about zero up to about three times and preferably up to about twice the amount of polymer present in the composition.

The additive that may subsequently be disposed in the cells and/or walls of the foamed structure can be in solution in the propellant, or dispersed in the propellant, or in solution or in dispersion as a separate liquid phase that is itself dispersed in the propellant phase of the composition. The additive may also be the sole component of a separate liquid phase that is itself dispersed in the propellant phase of the composition. Thus, the propellant compositions of the invention can be solutions or emulsions in which the propellant is the solvent in the continuous phase and another liquid or liquid composition or solid which is the additive is dispersed therein in a discontinuous phase. Since the propellant boils at a temperature below 45° F., it is of course a vapor at room temperature and pressure. Consequently, the propellant compositions of the invention are stored in closed containers capable of withstanding the pressure of the propellant, so as to maintain the propellant in the liquid phase. When the composition is ejected from the container to atmospheric pressure at atmospheric (room) temperature, the propellant is rapidly volatilized, and a coherent foamed structure is formed, with the additive in the cells and/or walls.

Spitzer et al U.S. Pat. No. 3,912,666, patented Oct. 14, 1975, provides emulsified synthetic polymer propellant compositions of the oil-in-water type in which water is the continuous phase, and the solution of synthetic polymer in a propellant is the discontinuous phase. The essential components of these oil-in-water emulsions are an aqueous solution comprising a foam-stabilizing agent, which is the aqueous phase, and an oil phase consisting essentially of a polymer dissolved in liquefied propellant which is also a foaming agent. Thus, when the pressurized composition packaged in a container is expelled through a valve into the atmosphere, the liquefied propellant immediately volatilizes, and foams both the oil phase and the aqueous phase, causing them to expand and the polymer to precipitate, resulting in a foamed structure.

Spitzer et al U.S. Pat. No. 3,912,665, patented Oct. 14, 1975, provides synthetic polymer-propellant compositions in which an organic liquid that also may comprise a foaming agent or foam-stabilizing agent serves as the continuous or dispersing phase for a solution consisting essentially of a polymer dissolved in liquefied propellant, which is a foaming agent. The organic liquid is present in an amount greater than its solubility in the polymer propellant phase. In the case of water-soluble organic liquids, a minor amount of water may be added to reduce its solubility in the polymer propellant phase, and thus ensure the presence of an organic liquid phase. The organic liquid is a liquid at atmospheric temperature and pressure, whereas the propellant is a gas under these conditions. Thus, when the pressurized composition packaged in a container is expelled through a valve into the atmosphere, the liquefied propellant immediately volatilizes, and foams the propellant phase, causing it to expand and the polymer to precipitate, resulting in the foamed structure, with the organic liquid phase in the foam cells thereof.

As indicated in the disclosures of these patents, such synthetic polymer-propellant compositions can be prepared by blending the ingredients in individual aerosol cans, which are capped and pressurized in conventional fashion with the normally gaseous liquefied propellants. The individual packages are shaken or otherwise agitated until the polymer dissolves, and the composition is uniform. Heat can be used to increase the rate at which the polymer dissolves.

Nonetheless, the time required for complete dissolution of the polymer can be rather long. In many cases, the propellant solvates the polymer particles, forming a skin of relatively impenetrable gelled material on the surface of the particles, which slows down the rate of dissolution of the polymer material within the skin, in the interior of the particles. Even though abrasion by agitation may eventually strip off the skin, the time required may be too long to permit application of this approach in a commercial process.

In accordance with the present invention, it has been determined that the polymer particles can be dissolved very quickly, normally less than one minute, if the particles are coated with an inert solid material that is insoluble in the propellant phase at atmospheric temperature, and then dissolved in the propellant. It appears that the coating material inhibits the formation of the skin that otherwise resists penetration of the particles by propellant, and, if the coating material is also a surfactant, assists in the dissolution by aiding in dispersion of the coated polymer particles in the propellant.

The process is of particular application for preparing synthetic polymer-propellant compositions in situ in closed containers capable of withstanding an internal pressure sufficient to keep the propellant in the liquid phase at atmospheric temperature. When the composition is withdrawn from such a container and reduced to atmospheric pressure, the propellant volatilizes rapidly, and a foamed structure is formed within a few seconds.

The coating material can be any inert material that is a solid at atmospheric temperature and is insoluble in the propellant phase.

The preferred materials are not wetted by water, but materials that are wetted by water can also be used and still more preferred are the inert solid materials that have surfactant properties as well.

Among the classes of materials which can be used are the water-soluble or water-dispersible gums, such as gum arabic, gum tragacanth, gum acacia, guar gum, and the galactomannans; water-soluble or water dispersible cellulose ethers and esters, including methyl cellulose, hydroxyethyl cellulose, ethyl hydroxyethyl cellulose, hydroxypropyl cellulose, and sodium carboxymethyl cellulose; hydrocarbon waxes including paraffin and microcrystalline wax; polyoxyalkylene glycols and glycol ethers that are waxes such as polyoxyethylene glycol, polyoxypropylene glycol, polyoxybutylene glycol, mixed polyoxypropylene-oxyethylene glycols and ethers, and mixed polyoxyethylen-oxybutylene glycols and ethers (the Pluronics), and the finely-divided solid materials normally used as fillers for synthetic polymers, including chalk, talc, graphite, silica, diatomaceous earth, clay, asbestos, magnesium silicate, calcium silicate, and magnesium stearate, aluminum stearate, kaopolite, powdered polyethylene and powdered polystyrene; magnesium carbonate, and magnesium trisilicate, as well as starch and starch derivatives.

An especially preferred class of coating materials, because they also have surfactant properties, are the metallic soaps, which are metal salts, such as alkali metal (sodium, potassium), alkaline earth metal (calcium, strontium and barium), and other polyvalent metal salts (magnesium, zinc, aluminum, tin, nickel, iron, cobalt, and lithium), of the saturated and unsaturated higher aliphatic carboxylic acids, sulfuric acids, sulfonic acids and phosphoric acids having from about nine to about twenty-six carbon atoms in the aliphatic group, such as capric, caprylic, lauric, myristic, palmitic, stearic, oleic, linoleic, arachidic, behenic, margaric, tridechoic, and cerotic carboxylic acids, sulfonic acids, sulfuric acids and phosphoric acids, and the mixtures of such carboxylic acids naturally occurring in fats, oils, waxes and rosins, such as the soaps of coconut oil fatty acids, tallow fatty acids, lard fatty acids, fish oil fatty acids, beeswax, palm oil, fatty acids, sesame oil fatty acids, peanut oil fatty acids, olive oil fatty acids, palm kernel oil fatty acids, corn oil fatty acids, babassu oil fatty acids, rosin acids, abietic acid, and greases.

It is important that the coating material not be soluble in the propellant phase, or any component of the propellant phase or synthetic polymer-propellant composition. If, for example, the propellant phase includes water, then a water-soluble coating material should not be used; a water-insoluble material is however satisfactory, in such a case.

The coating material may be applied to the particles of polymer simply by blending the two particulate materials together. Preferably, the coating material is in a more finely-divided particulate form than the polymer, but the particle size is not critical, and can be within the range from about 0.01 to about 200 microns. If the composition is packaged in a conventional 4 to 12 oz aerosol container, however, the coating material preferably has a particle size below about 50 microns, to avoid clogging of valves in such aerosol containers.

It is also possible to apply all or part of the coating material to the polymer particles as a liquid, for example, a solution or dispersion of the coating material in a liquid solvent or suspending agent in which the coating material is insoluble, but the liquid solvent or suspending agent should not be a solvent for the polymer. After coating the polymer particles, the liquid should be removed, insofar as possible, so as to deposit the coating material on the surface of the polymer particles. If the liquid is immiscible with or insoluble in the propellant phase, it is not necessary that all of the liquid be removed. Alternatively, instead of removing the liquid, the polymer particles may be dusted with additional solid coating material.

Liquid dispersing agents that can be used include mineral oils, vegetable oils, silicone oils, propylene glycol, glycerine, water, and aqueous solutions of surfactants.

If desired, the polymer particles can first be coated with a liquid which is inert to and insoluble in the polymer, and then the coating material applied. The presence of the liquid will assist in bonding the coating material to the particles of polymer. In such cases, an amount of liquid within the range from about 0.01 to about 100 parts per 100 parts by weight of polymer can be used. Preferably, the amount is within the range from about 2 to about 50 parts of liquid per 100 parts of polymer.

After application of any liquid and the coating material, the polymer particles should be free-flowing. If the polymer particles are not free-flowing, then additional coating material should be added, until they are.

In applying the process to synthetic polymer-propellant compositions, it is necessary to keep the propellant in the liquid phase, which means of course that the composition must be held under superatmospheric pressure. Thus, the process is carried out under pressure.

If a pressurized container is to be used to dispense the synthetic polymer-propellant composition, the coated polymer can be introduced into the container in the form of the free-flowing powder. The other ingredients of the composition are introduced into the container, and the propellant is added last. If the pressurized container is then promptly agitated, the polymer will dissolve in less than about one minute, normally.

If the container is not agitated promptly after the addition of propellant, dissolution is slower, but the polymer can still be dissolved in one day or at most, several days, and with minimum effort. The propellant slowly converts the particles into a soft, flowable mass, which becomes progressively more fluid. After about a day, the mass will have become sufficiently fluid that slight shaking is sufficient to obtain a uniform dissolution of polymer in the liquid propellant.

After the polymer particles have dissolved in the propellant phase, the coating material, because it is a solid insoluble in the propellant phase, will tend to settle out in particulate form. if the composition is packaged in a conventional 4 to 12 oz aerosol container, and the container is shaken before expelling the synthetic polymer-propellant composition, such particles will of course be redispersed, and can then be expelled with the synthetic polymer-propellant phase. Accordingly, when such containers are used, the particle size of the coating and surfactant materials should be small enough to avoid interfering with expulsion of the synthetic polymer-propellant composition. This will of course depend upon the type of composition and the valve system used in the container, but generally in this case the particle size should be less than about 50 microns.

Because the coating material remains behind after dissolution of the polymer particles, it is also important that they remain free-flowing, and not pack or agglomerate to form larger particles, which can cause clogging difficulties in the fluid delivery system. Coating materials that are not wetted by water show little or no tendency to pack or agglomerate after polymer particle dissolution.

In general, the amount of coating material required is rather small, but it does depend upon the surface area of the polymer particles. Usually, an amount within the range from about 2% to about 40% by weight of polymer particles having a particle size within the range from about 50 to about 2000 microns will give good results. Preferably, the amount is within the range from about 5% to about 20% by weight of the polymer particles.

If the coating material does not have surfactant properties, a surfactant can be added, to improve dissolution rate. The surfactant should not be soluble in the propellant phase, although this is not a prerequisite.

Typical satisfactory anionic surfactants are the alkyl sulfates, such as sodium lauryl sulfate; the alkyl aryl sulfonates, such as sodium polypropylene benzene or toluene sulfonates and the sodium keryl benzene or toluene sulfonates; the sulfated ethoxynated phenols, such as the ammonium salt of sulfated ethoxynated nonyl phenol, prepared by condensation of nonyl phenol with five moles of ethylene oxide; the sodium fatty acid esters of taurine, such as sodium palmitic or oleic methyl tauride or mixtures thereof; the esters of higher fatty acids and hydroxy ethane sulfonates, such as oleic acid ester of hydroxy ethane sodium sulfonate; sodium lauroyl sarcosinate; sodium stearoyl lactate; sodium lauroyl lactate; sodium dioctyl sulfosuccinate; sodium lauroyl isethionate, and sodium lauryl sulfoacetate. Also useful are nonionic surfactants, such as the polyethylene glycol esters of the higher fatty acids, for example, polyethanoxy esters of lauric, myristic, palmitic and stearic acids, polyethanoxy ethers of lauryl alcohol, cetyl alcohol, oleyl alcohol and lanolin alcohol, the polyethanoxy ethers of alkyl phenols, such as the condensation product of octyl and nonyl phenol with five to fifty moles of ethylene oxide; the higher fatty acid esters of sorbitan-ethylene oxide condensates, such as the polyethanoxy esters of sorbitan monostearate; polyethanoxy-polypropanoxy polyols. Cetyltrimethylammonium bromide is a typical cationic surfactant.

The amount of surfactant can be very small, since very small amounts serve a good dispersing function. An amount within the range from about 0.001% to about 10% by weight of the polymer particles is satisfactory. Preferably, the amount is within the range from about 0.01 to about 1% by weight of the polymer particles.

The process of the invention is applicable to any of the propellant compositions of any U.S. Pat. Nos. 3,912,667, 3,912,666 and 3,912,665, the disclosures of which are accordingly hereby incorporated by reference. Thus, the propellant compositions of the invention can be homogeneous solutions, in which all of the components present are soluble in and/or miscible with each other. In this case, any additive that is present is dissolved in the propellant with the polymer, and is deposited in the cells of the structure when the propellant is volatilized as the structure is being formed. Any nonpropellant liquid will also be deposited in the cells, if it is insoluble in the polymer. Any additive dissolved in this liquid will be applied with the liquid from the cells of the structure when the foamed structure is used.

The propellant compositions of the invention can also be composed of two phases, in which event the phases are emulsified one in the other, with the polymer-propellant solution serving as the continuous phase. The discontinuous phase then can include, for example, a liquid solution which is the additive. When the propellant is volatilized, and the foamed polymer structure is formed, the initially emulsified droplets that comprise the additive solution are then deposited in the cells, as in the case of a propellant composition that is a homogeneous solution. Such emulsions can be composed of an aqueous phase dispersed in the polymer-propellant solution or an organic liquid phase dispersed in the polymer-propellant solution. It is referred in such emulsions that the continuous phase be the polymer-propellant solution.

A solid additive can also be dispersed in the polymer-propellant solution. It will be deposited in the cells and walls of the structure when the structure is formed. Preferably, the solid additive is water-soluble and can be extracted by soaking the structure with water.

Emulsifying agents can be added in order to obtain a reasonably stable emulsion, to ensure uniformity while a portion of the material is being withdrawn from the container and converted to a foamed structure. The emulsifying agents used favor the formation of an emulsion in which the polymer-propellant solution is the continuous phase. However, long-term stability of these emulsions is generally not required. It is sufficient for the formation of a satisfactory structure that the emulsion be capable of being made uniform and sufficiently stable by hand shaking, so as to retain such uniformity when a portion of the material is expelled.

The types of emulsifiers that can be used are usually organic. They may be cationic, anionic, or nonionic. Emuslfiers are also classified as hydrophobic or hydrophilic, hydrophobic emulsifiers tending to form emulsions in which the hydrophobic organic solvent phase, such as the polymer-propellant solution, is a continuous phase, and any aqueous system present is the discontinuous phase, while a hydrophilic emulsifier tends to form a continuous phase of the aqueous portion, with the organic portion being discontinuous. In general, mixtures of hydrophobic and hydrophilic emulsifiers are employed since it is possible to obtain more stable emulsions with such mixtures than with a single emulsifier. The preferred ratio of hydrophobic to hydrophilic emulsifier will depend upon the nature of the liquid that is to be emulsified. Thus, if the liquid is predominantly water, a more hydrophobic ratio is preferred than would be the case if the liquid were a polar organic liquid such as ethanol, glycerine or propylene glycol. Organic liquids that are not sufficiently polar to be soluble in water and that separate from the polymer-propellant solution ordinarily form reasonably stable emulsions without need for the incorporation of emulsifying agents.

Accordingly, the invention is applicable to emulsified propellant compositions that include a synthetic polymer in solution in a low boiling propellant, dispersed or emulsified in an organic liquid as the continuous phase, and/or dispersed in an oil in water emulsion.

The process can be applied to any thermoplastic polymer, as disclosed in U.S. Pat. Nos. 3,912,667, 3,912,666 and 3,912,665, that can be rendered in powdered or granular form, and that can be dissolved in a liquefied propellant, alone or with the aid of one or more solvents or materials that show solvent properties in the combination, or a surfactant, as indicated above, and that is also film-forming, so that it tends to form a cohesive mass upon evaporation of a propellant solution thereof.

Thermoplastic polymers as a class, thermosetting polymers in a propellant-soluble stage of polymerization, and propellant-soluble polymers capable of being cross-linked, can be used. The polymerization or cross-linking of the latter two types of polymers can be effected during or after the structure has been formed, to set the structure. Alkyl acrylate and alkyl methacrylate polymers and copolymers, such as ethyl methacrylate, butyl methacrylate, isobutyl methacrylate, 50/50 n-butyl/isobutyl methacrylate copolymer, 25/75 lauryl-/isobutyl methacrylate copolymer, 30/70 stearyl/t-butyl methacrylate copolymer, 50/50 ethyl/n-butyl methacrylate copolymer, copolymers of acrylic and vinyl compounds, such as 50/50 vinyl toluene/isobutyl methacrylate copolymer, 50/35/15 vinyl toluene/t-butyl methacrylate/stearyl methacrylate terpolymer, 50/50 ethyl acrylate/vinyl acetate copolymer, certain other vinyl polymers, such as polyvinyl acetate, vinyl toluene-butadiene copolymers, carboxylated vinyl acetate, certain cellulose derivatives, such as ethyl cellulose, cellulose acetate, cellulose propionate, cellulose acetate butyrate and cellulose acetate propionate, and certain silicone polymers such as Silicone XC-20997, are soluble in propellants of the class set forth.

Polymers which can be set to a solvent-insoluble stage of polymerization chemically or by radiation include urethane prepolymers, unsaturated polyesters such as unsaturated alkyd polymers, and polyolefins such as polybutylene and poly-2-methylbutene-1.

The polymer should have a molecular weight within the range from about 10,000 to about 1,000,000. Polymers of molecular weight below about 10,000 may not have sufficient cohesive strength to form a cohesive foamed structure, while those with molecular weights in excess of about 1,000,000 may be insoluble in propellant solvents. Polymers having molecular weights within the range from about 25,000 to about 600,000 are preferred.

As the propellant, there can be used in the compositions of the invention any volatile organic compound that has a boiling temperature below 45° F. at atmospheric pressure, and that is chemically inert to the synthetic resin and the additive that may be present in the compositions. Thus, hydrocarbons such as propane, n-butane and isobutane can be employed, as well as halogenated hydrocarbons such as vinyl chloride, methyl chloride, methyl bromide, dichlorodifluoromethane (Propellant 114), 1-chloro-1,1-difluoroethane (Propellant 142B), 1,1-difluoroethane (Propellant 152A), chlorodifluoromethane (Propellant 22), 1 chloro-1,1-difluoro-2,2-trifluoroethane (Freon 115), octafluorocylobutane (Freon C 318), a mixture of dichlorodifluoromethane and 1,1-difluoroethane (Freon 500), a mixture of chlorodifluoromethane and 1-chloro-1,1-difluoro-2,2-trifluoroethane (Freon 502).

The relative proportions of propellant and polymer in the propellant compositions of the invention determine to a considerable extent the nature of the foamed structure that is formed, when the pressure upon the composition is reduced to atmospheric and the propellant allowed to volatilize rapidly. If the proportion of polymer is too low (and usually the lower proportion is not less than approximately 10% polymer by weight of the composition) a cohesive foamed structure is not formed, but instead a bubbly, sticky, flowable mass is obtained. If the material is expelled as a spray, through a fine orifice, a plurality of foamed particles are obtained, similar in some respects to the decorative particles obtained according to U.S. Pat. Nos. 2,716,637 and 2,773,855 referred to above. If the proportion of propellant is too low, various difficulties will be encountered, due to the high viscosity of the polymer-propellant solution, as well as to the toughness of the resultant foamed structure. For example, it will not only be difficult to expel the composition through a valve, but after use the valve is likely to clog or to seat itself improperly, so as to leak. Further, if an additive is present in a separate liquid phase, it will not only be difficult to obtain a reasonably stable emulsion of this phase in the propellant phase; if separation occurs, it will not be possible to effect reemulsification by hand shaking.

Usually, however, the composition may contain up to 50% by weight of polymer, before performance is seriously impeded by the high proportion of polymer, and sometimes as much as 60% polymer can be present, depending to some extent upon the molecular weight of the polymer and its solubility in the propellant that is used.

The amount of propellant is within the range from about 20% and to about 70% by weight of the composition, sufficient to form a coherent voluminous foamed structure containing open and/or closed cells upon rapid volatilization. The boiling point of the propellant is below 45° F. to ensure such rapid volatilization at atmospheric temperature and pressure. If volatilization is too slow, a coherent structure may not be formed rapidly, if at all, and for this reason propellants boiling at or above 45° F. are not suitable except in small amounts, as indicated below, in admixture with propellants boiling below 45° F.

In addition to the propellant and the synthetic polymer, the compositions can include additional less volatile or relatively nonvolatile solvents, which may be solvents or cosolvents for the polymer, or alternatively solvents for any additive that may be present, or which may be solvents for both the polymer and the additive. There may also be plasticizers for the polymer, coloring agents, fillers for the polymer which modify the polymer component of the foamed structure and a curing agent for the polymer, if the polymer is in a partially polymerized condition, so that polymerization can be completed after the foamed structure has been formed, to set the structure in a desired configuration.

It is usually preferred that liquid components of the propellant composition boiling at or above 45° F. that are not propellants and that act as solvents for the polymer not exceed about three times and preferably not exceed about twice the weight of the polymer present, and in most cases they should not exceed the weight of polymer present. In general, the amount of such solvent should also not be greater than the amount by weight of propellant present. However, the exact amount that can be tolerated will depend upon the concentration of polymer in the propellant composition, as well as whether the liquid is a good or poor solvent for the polymer.

Liquids which are higher boiling than the propellant will modify the foamed structure. If they are also solvents for the polymer they may also plasticize the polymer during the period after the propellant has been volatilized, and before the remaining less volatile solvent is fully volatilized. Such a transitional plasticized stage can be useful in forming the foamed structure into a desired configuration, and it may also aid in the formation of a higher proportion of closed or nonruptured cells.

Examples of solvents that boil above 45° F. include dichlorofluoromethane, trichlorofluoromethane, 1,1,2-trichloro-1,2,2-trifluoroethane, 1,2-dibromo-1,1,2,2-tetrafluoroethane, 1,1,2,2-tetrachloro-1,2-difluoroethane, methanol, ethanol, acetone, methyl isobutyl ketone, benzene, toluene, xylene, chloroform, methylchloroform, methylene chloride, 1,1,1-trichloroethane, and perchloroethylene.

Plasticizers can also be incorporated. These are selected according to the nature of the polymer, and since they are nonvolatile permanently soften the foamed structure.

Plasticizers which may be useful include butyl phthalyl butyl glycolate, tributyl citrate, acetyl tributyl citrate, tricresyl phosphate, dibutyl tartrate, dibutyl phthalate, di-2-ethylhexyl azelate, chlorinated biphenyl and methyl abietate.

Fillers for the polymer can be used as extenders for the polymer, and may also modify the physical properties of the foamed structure. The filler usually has a small particle size, although fibrous material also can be used. Satisfactory fillers include chalk, talc, silica, diatomaceous earth, clay, asbestos, magnesium silicate, calcium silicate, magnesium stearate, kaopolite, powdered polyethylene and powdered polystyrene. The filler can be from 0 to 300% by weight of the resin. Coloring agents including dyes and pigments are used in small proportions, ranging from 0 to 10% by weight of the resin.

Any additive that is not attacked by the propellant or polymer can be incorporated in the propellant compositions of the invention, and is present in an amount in excess of that which is dissolved in the polymer (if any) after the propellant has been volatilized, and the additive will remain in the foamed polymer structure after the propellant has been volatilized. The additive will always be found in the cells after the structure is formed. If a liquid is present in the cells too, and the additive is soluble in the liquid, an additive solution is present in the cells. If, in addition, the additive is compatible with or soluble in the polymer, it will be found in the polymer matrix as well, and this is particularly so when the additive is a solid and no liquid is present. The liquid if present will also permeate the polymer if it is soluble therein, and any additive solution therein will do the same, if this be so. Incompatability of the additive with the polymer can be ensured by providing a liquid solvent for the additive that is itself incompatible with the polymer, thus ensuring that the additive is dissolved in the solvent, and the resulting solution is found in the cells of the structure.

Apart from these requirements, which are purely physical, any type of additive can be employed, depending upon the intended use for the structure.

The foamed structures of the invention, for example, are particularly useful as applicator pads for external or topical application of cosmetics of all types, such as those intended for cleansing, conditioning, lubricating, and protecting the skin, hormone preparations, suntan preparations, skin lighteners and bleach creams, foundation makeups, eye makeups, pre-shave and after-shave preparation, depilatories, hair grooming preparations, permanent wave preparations, hair straightening preparations, anti-dandruff preparations, bath preparations, nail lacquers and removers, antiperspirants and deodorants, fragrance-imparting preparations, perfumes, baby toiletries, and hypoallergenic cosmetics. They are also useful applicators for soap and synthetic detergent preparations of all types for personal washing, laundering, dishwashing, cleansing of silver, shampoos, shaving soaps and creams, hair colorings and dye removers, wave sets, lacquers, rinses and conditioners, and dry shampoos. They are also useful applicators for medicaments of all types, antimicrobial agents, such as bactericides and antifungal agents of all types, and antibiotics, for external application, such as topical or rectal, for instance, as suppositories.

The structures are also useful for furniture polish, shoe polish and furniture and shoe cleaners, floor cleaners, automobile cleaners and polishes, and porcelain, tile and plastic cleaners. When abrasives are included as the additive, they can serve as abrasive pads and scouring pads.

Exemplary medicaments that can be combined in the propellant compositions of the invention include the antihistamines; sulfa drugs, for example, sulfadiazine, sulfabenzamide, sulfacetamide, sulfanilamide, sulfapyridine, sulfathiazole, sulfapyrazine, sulfaguanidine, sulfaphthalidine, sulfasuxidine, sulfaoxazole, sulfamylon, phthalylsulfacetamide, $N'$-3,4-dimethylbenzoylsulfanilamide, benzylsulfanilamide and $N'$-2-(2-quinoxalyl) sulfanilamide; lipotropic agents, such as methionine, choline, inositol and betasitosterol and mixtures thereof; local anesthetics, such as benzocaine and pramoxine hydrochloride; essential oils, such as menthol, eucalyptus oil and eugenol; salts of penicillin, such as potassium penicillin G, procaine, penicillin G, 1-ephenamine penicillin G, dibenzylamine penicillin G, and other penicillin salts disclosed in U.S. Pat. No. 2,627,491; phenoxymethyl penicillin and salts thereof; additional antibiotic agents, such as streptomycin, dihydrostreptomycin, bacitracin, polymixin, tyrothricin, erythromycin, chlortetracycline, oxytetracycline, tetracycline, oleandomycin, chloramphenicol, magnamycin, novobiocin, cyclosterine and neomycin; vitamins, for instance, Vitamins A, $A_1$, $B_1$, $B_2$, $B_6$, $B_{12}$, and members of that family, folic acid and members of that family, and vitamins C, $D_2$, $D_3$ and E; hormones, such as cortisone, hydrocortisone, 9-α-fluorocortisone, 9-α-fluorohydrocortisone, prednisone and prednisolone; anabolic agents, such as 11, 17-dihydroxy-9-α-fluoro-17-o-methyl-4-androsten-3-one and 17-α-ethyl-19-nortestosterone; and additional antimicrobial agents, such as mycostatin, mercurichrome, iodine, methiolate, hexachlorophene, tribromosalicylanilide, trichlorocarbanilide, and undecylenic acid.

These medicaments can be compounded in the forms of solutions and elixirs with suitable solvents and dispersants, such as are conventionally used in such formulations. Aqueous and alcoholic solutions usually are used. The amount of medicament is not critical and is chosen to meet the need; usually, from 0.02 to about 15% is adequate.

Cleansing compositions can be formulated containing single or multiple detergents, such as soaps and anionic synthetic detergents or soaps and nonionic synthetic detergents, or they can be composed wholly of synthetic detergents, including the anionic, cationic and nonionic types. As used herein the term "detergent" includes soaps and synthetic detergents, including the anionic, cationic and nonionic types.

Typical satisfactory anionic nonsoaps are the alkyl sulfates, such as sodium lauryl sulfate; the alkyl aryl sulfonates, such as sodium polypropylene benzene or toluene sulfonates and the sodium keryl benzene or toluene sulfonates; the sulfated ethoxynated phenols, such as the ammonium salt of sulfated ethoxynated nonyl phenol, prepared by condensation of nonyl phenol with five moles of ethylene oxide; the sodium fatty acid esters of taurine, such as sodium palmitic or oleic methyl tauride or mixtures thereof; the esters of higher fatty acids and hydroxy ethane sulfonates, such as oleic acid ester of hydroxy ethane sodium sulfonate; sodium lauroyl sarcosinate; sodium stearoyl lactate; sodium lauroyl lactate; sodium dioctyl sulfosuccinate; sodium lauroyl isethionate, and sodium lauryl sulfoacetate. Also useful are nonionic nonsoaps, such as the polyethylene glycol esters of the higher fatty acids, for example, polyethanoxy esters of lauric, myristic, palmitic and stearic acids, polyethanoxy ethers of lauryl alcohol, cetyl alcohol, oleyl alcohol and lanolin alcohol, the polyethanoxy ethers of alkyl phenols, such as the condensation product of octyl and nonyl phenol with five to fifty moles of ethylene oxide; the higher fatty acid esters of sorbitanethylene condensates, such as the polyethanoxy esters of sorbitan monostearate; polyethanoxypolypropanoxy polyols. Cetyltrimethylammonium bromide is a typical cationic nonsoap.

The term "soap" as used herein refers to alkali metal, ammonium, and amine soaps of the saturated and unsaturated higher fatty acids having from about eight to about twenty-six carbon atoms, such as capric, caprylic, lauric, myristic, palmitic, stearic, oleic, linoleic, linolenic, arachidic, behenic, margaric, tridechoic, and cerotic acids and the mixtures of such acids naturally occurring in fats, oils, waxes and rosins, such as the soaps of coconut oil fatty acids, tallow fatty acids, lard fatty acids, fish oil fatty acids, beeswax, palm oil fatty acids, sesame oil fatty acids, peanut oil fatty acids, olive oil fatty acids, palm kernel oil fatty acids, corn oil fatty acids, babassu oil fatty acids, rosin acids, abietic acid, and greases.

Cleaning and abrasive compositions can also contain as additives water-soluble alkaline salts, including sodium silicate, borax, sodium carbonate and trisodium phosphate. Sequestering agents that are soluble in water, such as sodium hexametaphosphate, pentasodium tripolyphosphate, tetrasodium pyrophosphate, and the sodium salts of ethylenediaminetetraacetic acid or nitrilotriacetic acid, can also be used as additives, alone or with cleaning and scouring compositions.

When soaps or synthetic detergents are included in the polymer-propellant composition for the purpose of cleaning, other ingredients may also be present, such as sequestering agents, abrasives, foam boosters, and conditioning agents. These components may be present in the propellant composition in the form of a dispersed powder or dispersed liquid. The cleaning components may also be dissolved in a liquid that is emulsified in the polymer-propellant solution. However, the type and quantity of liquid used must be selected with care. For example, soaps and synthetic detergents that are effective water-soluble cleansing agents are also hydrophilic emulsifying agents and exhibit a pronounced tendency to form emulsions in which water is the continuous phase. To avoid this situation, which can result in the failure to form an applicator pad, the proportion of water present in the liquid phase containing the soap or synthetic detergent should be quite low, or the phase volume should be small as compared with the volume of the polymer-propellant solution. Often, it is advantageous to employ the cleaning components in the form of a powder dispersed in the polymer-propellant solution. After forming the foam structure, the cleaning agents are made available by soaking the applicator pad in water.

Germicidal detergent compositions can also be formulated, including, for instance, the 2,2'-dihydroxyhalogenated diphenyl methanes, such as G-11.

In one form of this invention, a co-dispensing valve may be used. Such valves are capable of simultaneously mixing and dispensing materials from two separate compartments. Thus, one compartment would contain the pad-forming composition and the other would contain the cosmetic or other additive. In this instance, somewhat more leeway is possible regarding the formulation of the additive preparation. However, if the latter contains too hydrophilic an emulsifier system, an applicator pad is not likely to form. Similarly, components of the additive that are likely to dissolve the polymer foam structure rapidly should be avoided.

The polymer-propellant compositions of the invention are converted into foamed polymer structures when the propellant is permitted to volatilize. This is easily accomplished, with almost immediate volatilization of most of the propellant, by storing the propellant composition in a closed container when the autogenous pressure is sufficient to maintain the propellant in the liquid phase, and then rapidly reducing the pressure to atmospheric pressure at room temperature, whereupon the propellant rapidly volatilizes and the foamed structure is formed. The propellant composition may also be stored in a closed container, under applied pressure greater than the autogenous pressure arising from the propellant itself to facilitate expelling the composition from the container, as through a valve or orifice, into the atmosphere. Because of the high volatility of the propellants employed, the polymer structure is nonsticky, unless a plasticizer or other nonpropellant solvent for the polymer is also present in sufficient amount to impart a sticky characteristic to the polymer. If the structure is to be adhered to a surface, stickiness can be desirable. In the case of a solvent that also volatilizes, although more slowly than the propellant, this sticky condition is transitory, however, and exists only until the solvent has been removed. Excessive stickiness is undesirable in an applicator pad. In general, the organic liquids used to form the continuous phase of the emulsion act as lubricants and thus prevent stickiness.

If a composition formulated to produce a pad with a high proportion of closed cells is ejected into a confined space, such as a mold, preferably closed, the foamed structure will acquire the configuration of the mold, and a molded object is obtained. The molding can be carried out at room temperature, without application of external pressure, since a pressure sufficient to ensure that the structure conforms to the configuration of the mold is obtained upon volatilization of the propellant at atmospheric pressure and temperature.

If the emulsified composition is ejected into the atmosphere, the foamed structure will have an irregular shape. It is quite convenient, in practicing this embodiment of the invention, simply to eject the composition from the container into the hand, forming a pad of any desired size, which is controlled by controlling the duration of the ejection period. For this purpose, the polymer-propellant compositions of the invention are suitably packaged in aerosol containers of the standard type, the valve being controlled by one hand, and the foamed structure being received in the other. The foamed structure is formed almost instantaneously, and the applicator pad is ready for use within seconds after the procedure has begun. The structure is shape-retaining because of the nature of the polymer used, and it is also flexible initially because of the retention of some propellant, even if no plasticizer is present, i.e., if the polymer is a rigid polymer.

Alternatively, the valve actuator may be shaped as a dish or a hemisphere so that it acts as a receptacle or mold for the foamed structure as it is being formed, and the interior shape of the receptacle or mold determines the shape of the foamed structure.

The compositions can be stretched to some extent and compacted as the foamed structure is being formed, and in this way can be made to conform to the shape of the object upon which it is being applied, so as to form a covering or a coating. When applied to the body, for example, a coating including a medicament for release to the skin can be formed, which can be allowed to remain in contact with the skin for long periods, for slow release of the medicament over a long period of time. However, because the compositions are so rapidly converted into a foamed structure, they are not actually flowable, and will not spread voluntarily. In this respect, they differ from conventional aerosol paints or lacquers, from which the solvent is removed only slowly, and which are consequently flowable, and can be spread out to a film that may be only a few mils thick, and they also differ from the spreadable compositions described in U.S. Pat. No. 3,419,506 to Gander.

Prior to expulsion from the container, however, the compositions are flowable. The viscosity of the fluid composition is in no way critical, provided the composition is sufficiently flowable to be ejected from the container under pressure. The viscosity, accordingly, can range from a thin, quickly flowable liquid, to a rather thick, barely flowable, thixotropic or gel-like composition.

When the composition is homogeneous, or the dispersed phase remains uniformly distributed throughout the composition, the viscosity may be as high as 1,000,000 cp at atmospheric temperature. However, when the composition is likely to undergo settling or layering and it is necessary to shake before expelling a portion of the contents, it is necessary that the viscosity not exceed about 50,000 cp, and preferably it should be less than 10,000 cp, at atmospheric temperature.

In the event that the propellant employed in the compositions of the invention has a sufficient vapor pressure at ambient temperature, it will also serve as a propellant to expel the material from the pressurized container in which it is confined. In the event that its vapor pressure is insufficient, additional pressure may be provided in the container by a suitable pressurizing gas, such as nitrogen, nitrous oxide or carbon dioxide. Because commercial regulations limit the total pressure of common aerosol containers to not more than about 150 psig, the propellant employed is preferably one whose vapor pressure in the propellant does not exceed this limit.

The following Examples represent preferred embodiments of the invention in the opinion of the inventors:

EXAMPLE 1

This Example illustrates a polymer-propellant composition that forms an applicator pad suitable for use with water as a mild lathering facial cleanser.

Two compositions were prepared; a Control in which the polymer particles were not coated as in the invention, and an Example in which the particles were coated, using glyceryl trioleate to aid in adhering the coating material to the polymer particles. The coating materials used were the coconut fatty acid ester of sodium isethionate and pyrogenic silica of which enough silica was added to obtain a free-flowing powder. The formulations were as follows:

|  | Parts by Weight | |
|---|---|---|
|  | Control A | Example 1 |
| Ethyl methacrylate polymer[1] | 10.6 | 10.4 |
| Coconut fatty acid ester of sodium isethionate | 8.5 | 8.3 |
| Glyceryl trioleate | 10.6 | 10.4 |
| Tributyl citrate | 4.3 | 4.2 |
| Pyrogenic silica | — | 2.1 |
| 1,1,1-Chlorodifluoroethane | 66.0 | 64.0 |

[1]About 400,000 molecular weight; particles less than 100 microns in diameter

In preparing the Control composition, the detergent and polymer powders were separately poured into a glass pressure bottle, after which a mixture of glyceryl trioleate and tributyl citrate was added. The valve was attached, and the propellant added through the valve. The container was shaken by hand for one minute. It was observed that about one-half of the polymer agglomerated. Next, the container was vigorously shaken, using a paint shaker, for ten minutes, but all of the agglomerates still had not dissolved at the end of this time.

In preparing Example 1, the polymer particles were blended with 1.5 parts of glyceryltrioleate, a liquid to aid in adhesion of the coating materials. Then the detergent powder, coconut fatty acid ester of sodium isethionate, was mixed in, followed by the silica. A free-flowing powder was obtained, in which the polymer particles were coated with glyceryl trioleate, silica, and the coconut fatty acid ester of sodium isethionate.

This powder was transferred to the same kind of glass pressure bottle as before, followed by addition of a mixture of the remainder of the glyceryl trioleate and the tributyl citrate. The valve was attached, and the propellant was added through the valve. The container was then shaken by hand for ten seconds. The polymer had dispersed at the end of this time and the increasing viscosity of the composition showed that the polymer was dissolving. After a few minutes, dissolution was complete, and an applicator pad could be obtained by expelling the composition through the open valve of the pressure bottle.

EXAMPLE 2

This Example illustrates a composition that forms an applicator pad suitable for use as an anhydrous hand cleaner. When the pad is rubbed on the hands, it gathers up dirt and greasy soils in a cleansing action.

Two compositions were prepared; a Control in which the polymer particles were not coated and Example 2, in which the polymer particles were coated with kerosene and zinc stearate. The formulations were as follows:

|  | Parts by Weight | |
|---|---|---|
|  | Control B | Example 2 |
| Polyvinyl acetate[1] | 15.6 | 15.2 |
| Kerosene, deodorized | 6.3 | 6.1 |
| Zinc stearate | — | 3.0 |
| Tributyl citrate | 6.2 | 6.0 |
| Isocetyl alcohol | 6.2 | 6.0 |
| 1,1,1-Chlorodifluoroethane | 65.7 | 63.7 |

[1]About 1 million molecular weight; particles 150 to 1000 microns in diameter

In the Control the polymer particles were transferred to a glass pressure bottle, and a mixture of kerosene, tributyl citrate and isooctyl alcohol was added. The valve was attached, and the propellant was added through the valve. The container was then shaken for one minute by hand. It was observed that about 75% of the polymer remained on the bottom of the bottle as an agglomerate. The next day the agglomerate remained. No change was noted by hand-shaking, but after the bottle had been shaken on a paint shaker for ten minutes, the polymer was mostly dissolved.

In Example 2, the polymer particles were mixed with the kerosene, a liquid to aid in adhering the zinc stearate to the polymer particles, and zinc stearate then added, resulting in a free-flowing polymer powder with the zinc stearate and kerosene coated on the polymer particles. The powder was transferred to the same kind of glass pressure bottle as before. The remainder of the kerosene, tributyl citrate and isocetyl alcohol were combined and added. The valve was attached, and the propellant was added through the valve. The container was then shaken by hand for twenty seconds. The polymer dispersed without clumping, and the increase in viscosity of the composition showed that the polymer was dissolving. After a few minutes, the polymer had dissolved, and an applicator pad could be formed by expelling the composition through the open valve of the bottle.

EXAMPLE 3

This Example illustrates a composition that forms an applicator pad suitable for use as an eye make-up remover.

Two compositions were made up; a Control in which the polymer particles were not coated in accordance with the invention, and an Example in which the polymer particles were coated with glyceryl trioleate and magnesium stearate. The formulations were as follows:

|  | Parts by Weight | |
| --- | --- | --- |
|  | Control C | Example 3 |
| Polyisobutyl methacrylate[1] | 30.5 | 28.6 |
| 10% Miranol C2M SF Conc. in water[2] | 2.5 | 2.4 |
| Glyceryl trioleate | 5.1 | 4.8 |
| Mineral oil | 14.0 | 13.2 |
| Ethanol | 7.6 | 7.2 |
| Magnesium stearate | — | 6.2 |
| Isobutane | 40.3 | 37.6 |

[1]About 150,000 molecular weight; particles under 200 microns in diameter
[2]Amphoteric disodium dicarboxylic coconut oil fatty acids imidazoline derivative In the Control, the polymer particles were transferred to a glass pressure bottle. An aqueous 3% solution of amphoteric disodium dicarboxylic coconut oil fatty acids imidazoline derivative solution in water was then combined with the ethanol and added to the polymer. This was followed by a mixture of the mineral oil and glyceryl trioleate. The valve was attached, and the propellant was added through the valve. The container was shaken by hand for one minute. Practically all of the polymer had agglomerated. Even after ten days, the polymer agglomerates could not be dissolved in the remainder of the propellant solution by hand shaking. Mechanical shaking with a paint mixer was required.

In Example 3, the aqueous solution of amphoteric disodium dicarboxylic coconut oil fatty acids imidazoline derivative was mixed with the polymer particles and then the magnesium stearate was added, resulting in a free-flowing powder in which the polymer particles were coated with the surfactant solution and magnesium stearate. The powder was transferred to the same kind of pressure bottle as before. The mixture of glyceryl trioleate and mineral oil was then added, followed by the ethanol. The valve was attached, and the propellant added through the valve. The container was shaken by hand for ten seconds. Almost all of the polymer dispersed and dissolved. A small agglomerate settled out, but this dissolved overnight, and hand-shaking for a few seconds then resulted in a uniform composition. Expulsion of the composition through the open valve resulted in the formation of an applicator pad.

EXAMPLE 4

This Example illustrates a composition that can be applied to the fingers or toes or other parts of the body to form a soft, protective covering useful as a protective bandage.

Two compositions were prepared; one Control in which the polymer particles were not coated in accordance with the invention, and one in which the polymer particles were coated with mineral oil and aluminum tristearate. The formulations were as follows:

|  | Parts by Weight | |
| --- | --- | --- |
|  | Control D | Example 4 |
| Ethyl cellulose, type T-10[1] | 28.5 | 26.1 |
| Aluminum tristearate | — | 8.7 |
| Mineral oil | 4.8 | 4.3 |
| Tributyl citrate | 4.8 | 4.3 |
| Ethanol | 4.8 | 4.3 |
| Isobutane | 47.6 | 43.5 |
| Dimethyl ether | 9.5 | 8.8 |

[1]Hercules, Inc. particles less than 300 microns in diameter

In the Control, the particles of ethyl cellulose were poured into a glass pressure bottle, after which the mineral oil and a mixture of the tributyl citrate and ethanol were added. The valve was attached, and a mixture of the two propellants, isobutane and dimethyl ether, was added through the valve. The container was shaken for one minute by hand. The polymer particles agglomerated, and settled to the bottom. The upper propellant layer was fluid. After three hours, the layers could not be dispersed into one layer by hand-shaking. A homogeneous solution resulted after shaking for ten minutes in a paint mixer.

In Example 4, the polymer particles were mixed with the mineral oil, a liquid to aid in adhering aluminum stearate to the polymer particles, and then the aluminum tristearate was mixed in, resulting in a free-flowing powder with the mineral oil and aluminum tristearate coated on the polymer particles. The powder was transferred to the same kind of glass pressure bottle as used before, and a mixture of tributyl citrate and ethanol was added. The valve was attached, and the mixture of the propellants was added through the valve. The container was shaken by hand for thirty seconds, giving an agglomerate-free viscous polymer solution containing dispersed aluminum tristearate. Expulsion of the composition onto the fingers resulted in a soft, protective coating closely adhering to the configuration of the fingers.

Having regard to the foregoing disclosure, the following is claimed as patentable and inventive embodiments thereof:

1. A process for preparing propellant compositions including a film-forming synthetic polymer that are capable of forming foamed structures containing open and/or closed cells which comprises coating the synthetic polymer in particulate form with an inert solid material insoluble in the propellant and in solutions of the synthetic resin in the propellant at atmospheric temperature; and then adding the propellant and dissolving the synthetic polymer in the propellant, thereby forming a synthetic polymer-propellant composition in situ.

2. A process according to claim 1 in which the process is carried out in a closed container capable of withstanding an internal pressure sufficient to keep the propellant in the liquid phase at atmospheric temperature, and when the composition is withdrawn from the container to atmospheric pressure, the propellant volatilizes rapidly and a foamed structure is formed within a few seconds.

3. A process according to claim 1 in which the synthetic polymer-propellant composition includes an additive which is deposited in the pores and/or walls of the foamed structure as the foamed structure is formed.

4. A process according to claim 3 in which the additive is in liquid form as a solution in a separate liquid phase that is itself dispersed in the propellant phase of the composition.

5. A process according to claim 3 in which the additive is an antiperspirant.

6. A process according to claim 3 in which the additive is an aqueous solution.

7. A process according to claim 3, in which the additive is in liquid form as a solution with the propellant.

8. A process in accordance with claim 3 in which the additive is in liquid form as dispersed in the propellant.

9. A process in accordance with claim 3, in which the additive is in liquid form as a separate liquid phase that is itself dispersed in the propellant phase of the composition.

10. A process in accordance with claim 9, in which the additive is an aqueous solution that is itself dispersed in the propellant phase of the composition.

11. A process according to claim 3 in which the additive is in liquid form as a dispersion in a separate liquid phase that is itself dispersed in the propellant phase of the composition.

12. A process according to claim 11 in which the separate liquid phase is an aqueous phase.

13. A process according to claim 3 in which an organic liquid solvent for the polymer is present in solution in the propellant phase.

14. A process according to claim 13 in which the organic solvent is a lower alkanol having up to three carbon atoms.

15. A process according to claim 3 in which the propellant is a hydrocarbon propellant.

16. A process according to claim 3 wherein the liquid propellant is inert to the synthetic polymer; wherein the additive is in liquid or solid form at atmospheric temperature and pressure in an amount in excess of any solubility of the additive in the polymer in the absence of the propellant, the additive being substantially inert to the synthetic polymer and to the propellant, the foamed structure being in a shaped form for immediate use as a pad from which the additive can be removed in liquid form by compression of the pad.

17. A process according to claim 3 in which the composition upon rapid volatilization of the propellant at atmospheric temperature and pressure forms a foamed polymeric structure which immediately is nonsticky, coherent, voluminous and self-supporting, which contains the additive, and which is in a shaped form for immediate use as a pad, from which the additive can be removed in liquid form by compression of the pad.

18. A process according to claim 17 in which the composition contains up to 50% by weight of the synthetic polymer.

19. A process according to claim 18 in which the polymer is dissolved in a liquid comprising, in addition to the liquid propellant, a solvent which has a boiling point above 45° F., said solvent being present in an amount not exceeding three times the weight of polymer and not exceeding the weight of propellant.

20. A process according to claim 18 in which the polymer is polyisobutyl methacrylate.

21. A process according to claim 18 in which the synthetic polymer is selected from the group consisting of cellulose derivatives, vinyl polymers and vinyl copolymers.

22. A process according to claim 21 in which the vinyl polymer is a methacrylate polymer or copolymer.

23. A process according to claim 21 in which the vinyl polymer is polyisobutyl methacrylate.

24. A process according to claim 3 in which the additive is selected from the group consisting of antimicrobial agents, coating compositions, fungistatic agents, fungicidal agents, abrasives, detergents, antibiotics, antiperspirants, medicaments, silicone oils, mineral oils and vegetable oils.

25. A process according to claim 1 in which the inert solid material is not wetted by water.

26. A process according to claim 25 in which the inert solid material is selected from the group consisting of water-soluble or water dispersible gums; water soluble or water-dispersible cellulose ethers and esters; hydrocarbon waxes; polyoxyalkylene glycols and glycol ethers; water-insoluble metallic soaps; and finely-divided fillers for synthetic polymers.

27. A process according to claim 26 in which the coating material is a water-insoluble metallic soap.

28. A process according to claim 25 in which the composition is packaged in a 4 to 12 oz aerosol container and the coating material has a particle size below about 50 microns, to avoid clogging of valves in the aerosol container.

29. A process according to claim 1 in which the coating material is applied to the particles of polymer by blending the two particulate materials together.

30. A process according to claim 1 in which the coating material is applied to the particles of polymer as a solution or dispersion of the coating material in a liquid solvent or suspending agent in which the coating material is insoluble, but which is not a solvent for the polymer.

31. A process according to claim 1 in which the polymer particles are coated with a liquid which is inert to and insoluble in the polymer, and then the coating material applied, the liquid bonding the coating material to the particles of polymer.

32. A process according to claim 31 in which the liquid is selected from the group consisting of mineral oil, vegetable oil, silicone oil, propylene glycol, glycerine, water, and aqueous solutions of surfactants.

33. A process according to claim 31 in which the liquid is in an amount within the range from 0 to about 100 parts per 100 parts by weight of polymer.

34. A process according to claim 1 in which the amount of coating material is within the range from about 2% to about 40% by weight of the polymer particles.

35. A process according to claim 1 in which the amount of coating material is within the range from about 5% to about 20% by weight of the polymer particles.

36. A process according to claim 1 in which the particle size of the polymer particles is within the range from about 50 to about 2000 microns.

* * * * *